(12) United States Patent
Burke et al.

(10) Patent No.: US 7,569,182 B2
(45) Date of Patent: *Aug. 4, 2009

(54) FILTER ASSEMBLY FOR A REPROCESSOR

(75) Inventors: Peter A. Burke, Concord, OH (US); Karl F. Ludwig, Girard, PA (US); Jude A. Kral, Twinsburg, OH (US); Francis J. Zelina, Lake City, PA (US)

(73) Assignee: American Sterilizer Company, Mentor, OH (US)

( * ) Notice: Subject to any disclaimer, the term of this patent is extended or adjusted under 35 U.S.C. 154(b) by 385 days.

This patent is subject to a terminal disclaimer.

(21) Appl. No.: 11/494,341

(22) Filed: Jul. 27, 2006

(65) Prior Publication Data

US 2006/0280647 A1    Dec. 14, 2006

Related U.S. Application Data

(63) Continuation-in-part of application No. 10/633,343, filed on Aug. 1, 2003, now Pat. No. 7,135,142.

(51) Int. Cl.
 *A61L 2/18* (2006.01)
(52) U.S. Cl. ............... 422/28; 422/24; 422/292; 73/38; 73/40
(58) Field of Classification Search ............ None
 See application file for complete search history.

(56) References Cited

U.S. PATENT DOCUMENTS

| | | | |
|---|---|---|---|
| 4,431,545 A | 2/1984 | Pall et al. | 210/641 |
| 4,617,065 A | 10/1986 | Sundheimer | 134/25.4 |
| 5,091,343 A | 2/1992 | Schneider et al. | 422/297 |
| 5,234,832 A * | 8/1993 | Disch et al. | 435/264 |
| 5,487,814 A | 1/1996 | Santasalo | 203/2 |
| 6,919,057 B2 | 7/2005 | Halstead et al. | 422/297 |
| 7,135,142 B2 * | 11/2006 | Burke et al. | 422/28 |

FOREIGN PATENT DOCUMENTS

| | | |
|---|---|---|
| EP | 0945140 A2 | 9/1999 |
| JP | 59-26116 | 2/1984 |
| JP | 4-55711 | 9/1992 |
| JP | 05-023551 | 2/1993 |
| JP | 07-008456 | 1/1995 |
| JP | 11128158 A | 5/1999 |
| JP | 2001-162284 | 6/2001 |
| JP | 2002-537105 | 11/2002 |
| WO | WO00/50158 | 8/2000 |

* cited by examiner

*Primary Examiner*—Elizabeth L McKane
(74) *Attorney, Agent, or Firm*—Kusner & Jaffe; Michael A. Centanni

(57) ABSTRACT

The present invention provides a method of operating a reprocessor that has a chamber for receiving items to be sterilized. The reprocessor is filled with water that has passed through a first and a second filter element that both comprise a filtration system. A liquid sterilant is generated by mixing the water with dry chemical reagents. The liquid sterilant is circulated through a fluid circulation system and the filtration system wherein a portion of the liquid sterilant is directed through a bypass conduit and another portion is directed through the first and second filter elements. After a predetermined exposure time, the reprocessor is drained. Then the reprocessor is filled with water for rinsing that has passed through the first and the second filter elements. The water for rinsing is heated prior to being introduced into the reprocessor.

41 Claims, 4 Drawing Sheets

FILTER ASSEMBLY FOR A REPROCESSOR

RELATED APPLICATIONS

The present invention is a Continuation-in-Part (CIP) of U.S. application Ser. No. 10/633,343 filed Aug. 1, 2003 now U.S. Pat. No. 7,135,142, entitled "Filter Assembly for a Reprocessor" which is incorporated herein by reference in its entirety.

FIELD OF THE INVENTION

The present invention relates to microbial deactivation of medical, dental, pharmaceutical, veterinary or mortuary instruments and devices, and more particularly to a filtration system for use in a liquid microbial deactivation system.

BACKGROUND OF THE INVENTION

Medical, dental, pharmaceutical, veterinary or mortuary instruments and devices that are exposed to blood or other body fluids require thorough cleaning and microbial deactivation or sterilization between each use. Liquid microbial deactivation systems are now widely used to clean and deactivate instruments and devices that cannot withstand the high temperatures of a steam sterilization system. Liquid microbial deactivation systems typically operate by exposing the medical devices and/or instruments to a liquid disinfectant or sterilization composition, such as peracetic acid or some other strong oxidant.

In such systems, the instruments or devices to be cleaned are typically placed within a chamber within the liquid microbial deactivation system, or in a container that is placed within the chamber. During a deactivation cycle, a liquid disinfectant is then circulated through a liquid circulation system that includes the chamber (and the container therein).

Following the deactivation cycle, a rinse solution, typically water, is circulated through the chamber to remove traces of the microbial deactivate and any particulate that may have accumulated on the instruments or devices during the deactivation cycle. As will be appreciated, it is important to have rinse water of high purity to insure that the microbially deactivated instruments and devices do not become re-contaminated during the rinse cycle.

The water used to rinse the instruments and devices generally passes through a filtration system to remove mycobacterium particulates from the water. Although small amounts of the liquid sterilant may back-up to the downstream side of the filtration system, the upstream contents of the filtration system are generally not microbially deactivated and/or sterile. Thus, there is a possibility that microbial contamination may accumulate in the upstream side of the filtration system over time, and subsequently pass into the downstream side of the filtration system and be introduced into the chamber during a rinse cycle.

The present invention overcomes these and other problems and provides an improved filtration system for filtering water used in a microbial deactivation system.

SUMMARY OF THE INVENTION

In accordance with one embodiment of the present invention, there is provided a method of operating a sterilizer having a chamber for receiving items to be sterilized, a fluid circulation system for circulating fluids through the chamber, means for generating a liquid sterilant from dry chemical reagents by mixing water therewith, and a water filtration system for filtering water entering the sterilizer. The filtration system includes a fluid feed line that is attached to the chamber, a directional valve disposed in the fluid feed line, and a first filter element in the fluid feed line. The first filter element is for filtering fluids therethrough and is located downstream of the directional valve between the directional valve and the chamber. A second filter element is disposed in the fluid feed line for filtering fluids flowing therethrough. The second filter element is located between the first filter element and the chamber. A water line is connected to the fluid feed line at an intersection located between the directional valve and the first filter element. A bypass line is connected to the fluid feed line to define a fluid path that bypasses the directional valve and the first and second filter elements. The method of operating comprises the steps of:

a) filling the sterilizer with water from a water source, by passing the water through the first and second filter elements;

b) generating a liquid sterilant by mixing water filtered by the first and second filter elements with the dry chemical reagents;

c) circulating the liquid sterilant through the fluid circulation system and the filtration system wherein a portion of the liquid sterilant is directed through the first and second filter elements, and a portion is directed through the bypass conduit;

d) draining the sterilizer after a predetermined exposure time;

e) passing water for rinsing through the first and second filter elements;

f) heating the water for rinsing after the water for rinsing has passed through the first and second filter elements; and g) introducing the water for rinsing into the chamber.

In accordance with another aspect of the present invention, there is provided a method of operating a reprocessor having a chamber for receiving items to be microbially deactivated, a fluid circulation system for circulating fluids through the chamber, means for generating a microbial deactivation fluid from dry chemical reagents by mixing water therewith, and a water filtration system for filtering water entering the reprocessor. The filtration system includes a fluid feed line that is connectable to a source of pressurized water, a first filter element, and a second filter element. The first filter element and the second filter element are disposed in the fluid feed line such that the second filter element is located downstream from the first filter element. A bypass line is connected to the fluid feed line to define a fluid path that bypasses the first and second filter elements. The water filtration system is connected to the fluid circulation system. The method of operating comprises the steps of:

a) filling the reprocessor with water from a water source, by passing the water through the first and second filter elements;

b) generating a microbial deactivation fluid by mixing water filtered by the first and second filter elements with the dry chemical reagents;

c) circulating the microbial deactivation fluid through the fluid circulation system and the filtration system, wherein a portion of the microbial deactivation fluid is directed through the fluid feed line and another portion is directed through the first and second filter elements;

d) draining the reprocessor after a predetermined exposure time;

e) filling the reprocessor with water for rinsing, by passing the water for rinsing through the first and second filter elements; and f) heating the water for rinsing prior to introduction of the water for rinsing into the chamber.

In accordance with another aspect of the present invention, there is provided a method of operating a reprocessor. The reprocessor has a chamber for receiving items to be microbially deactivated, a fluid circulation system for circulating fluids through the chamber, means for generating a microbial deactivation fluid from dry chemical reagents by mixing water therewith, and a water filtration system for filtering water entering the reprocessor. The filtration system includes a fluid feed line that is connectable to a source of pressurized water. A first filter element, a second filter element, and a heater are disposed in the fluid feed line such that the second filter element is downstream from the first filter element and the heater is downstream of the second filter element. A bypass line is connected to the fluid feed line to define a fluid path that bypasses the first and second filter elements and the heater. The water filtration system is connected to the fluid circulation system. The method of operating comprises the steps of:

a) filling the sterilizer with water from a water source, by passing the water through the first and second filter elements;

b) generating a liquid sterilant by mixing the filtered water with the dry chemical reagents;

c) circulating the liquid sterilant through the fluid circulation system and the filtration system, wherein a portion of the liquid sterilant is directed through the fluid feed line and another portion is directed through the first and second filter elements to produce filtered liquid sterilant; and d) operating the heater during the circulating step.

In accordance with yet another aspect of the present invention, there is provided a reprocessor having a circulation system for circulating a liquid sterilant or microbial deactivation fluid through a chamber that forms a part of the circulation system and a water filtration system for filtering water used in the reprocessor. The water filtration system includes a fluid feed line that forms a portion of the circulation system. One end of the fluid feed line is in fluid communication with the chamber. A directional valve is disposed in the fluid feed line. A first filter element is located upstream from the chamber and is disposed in the fluid feed line for filtering fluids flowing therethrough. A second filter element is disposed in the fluid feed line for filtering fluids flowing therethrough. The second filter element is located between the first filter element and the chamber. A water line is connectable to a source of pressurized water and is connected to the fluid feed line at a location between the directional valve and the first filter element. A bypass line is connected to the fluid feed line to define a fluid path that bypasses the first and second filter elements. The bypass line is connected at one end to the fluid feed line upstream of the directional valve and is connected at another end to the fluid feed line between the second filter element and the chamber.

In accordance with yet another aspect of the present invention, there is provided a sterilizer having a chamber for receiving items to be sterilized, a fluid circulation system for circulating fluids through the chamber, means for generating a liquid sterilant from dry chemical reagents by mixing water therewith, and a water filtration system for filtering water entering the sterilizer. The filtration system includes a fluid feed line that is attached to the chamber, a directional valve that is disposed in the fluid feed line, a first filter element disposed in the fluid feed line for filtering fluids therethrough. The first filter element is located downstream of the directional valve between the directional valve and the chamber. A second filter element is disposed in the fluid feed line for filtering fluids flowing therethrough. The second filter element is located between the first filter element and the chamber. A water line is connected to the fluid feed line at an intersection located between the directional valve and the first filter element. A bypass line is connected to the fluid feed line to define a fluid path that bypasses the directional valve and the first and second filter elements. The method of operating includes the steps of:

a) filling the sterilizer with water from a water source, by passing the water through the first and second filter elements;

b) generating a liquid sterilant by mixing water filtered by the first and second filter elements with the dry chemical reagents; and c) circulating the liquid sterilant through the fluid circulation system and the filtration system, wherein a portion of the liquid sterilant is directed through the first and second filter elements and a portion is directed through the bypass conduit.

In accordance with yet another aspect of the present invention, there is provided a reprocessor having a chamber for receiving items to be microbially deactivated or sterilized, a fluid circulation system for circulating fluids through the chamber, means for generating a microbial deactivation fluid from dry chemical reagents by mixing water therewith, and a water filtration system for filtering water entering the reprocessor. The filtration system includes a fluid feed line that is connectable to a source of pressurized water, a first filter element, and a second filter element. The first and second filter elements are disposed in the fluid feed line such that the second filter element is downstream from the first filter element. There is provided a method of checking the integrity of at least one of the filter elements that includes the steps of:

a) establishing a first known pressure on the upstream side of the filter element;

b) allowing pressure on the upstream side of the filter element to dissipate through the filter element and through a leak orifice of known dimensions;

c) monitoring over time the change in pressure on the upstream side of the filter;

d) establishing a second known pressure on the upstream side of the filter element;

e) allowing pressure on the upstream side of the filter element to dissipate through the filter element;

f) monitoring over time the change in pressure on the upstream side of the filter; and g) determining a flow rate through the filter based on the changes in pressure determined in steps c) and f).

One advantage of the present invention is the provision of a sterilizable water filtration system for a reprocessing system.

Another advantage of the present invention is the provision of a microbially deactivated filtration system for a microbial deactivation system.

Another advantage of the present invention is the provision of a filtration system as described above that reduces the likelihood of microbial contamination of a water supply as a result of microbial growth in a filter element.

A still further advantage of the present invention is a filtration system as described above that is capable of providing a high level of assurance that the water that is supplied downstream of the second filter element is microbially deactivated or sterile.

These and other objects will become apparent from the following description of one embodiment taken together with the accompanying drawings and the appended claims.

BRIEF DESCRIPTION OF THE DRAWINGS

The invention may take physical form in certain parts and arrangement of parts, one embodiment of which will be described in detail in the specification and illustrated in the accompanying drawings which form a part hereof, and wherein.

DETAILED DESCRIPTION OF THE INVENTION

Figure 1:
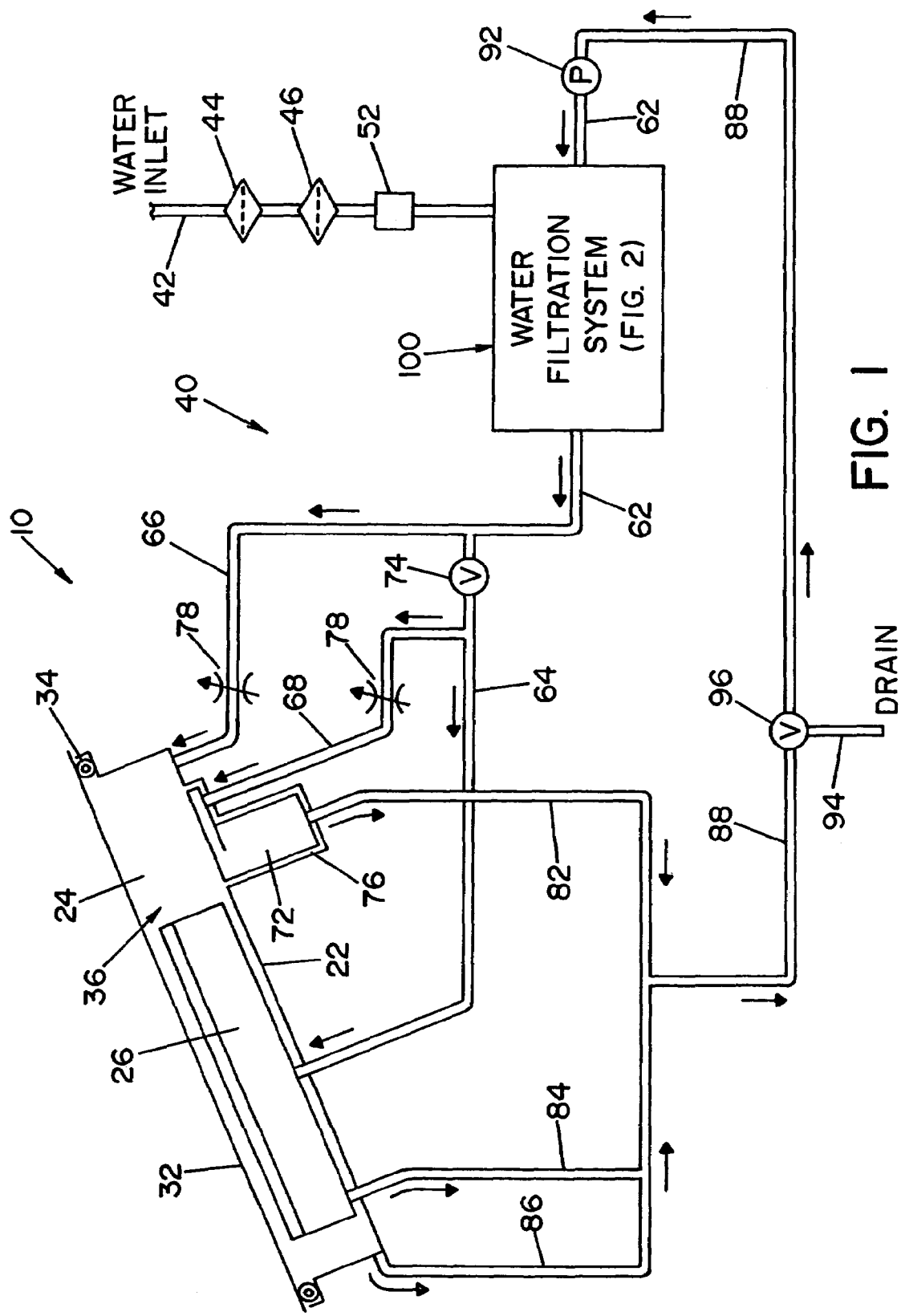
FIG. 1 is a schematic view of a microbial deactivation system.

Referring now to the drawings wherein the showings are for the purpose of illustrating one embodiment of the invention only, and not for the purpose of limiting same, FIG. 1 shows a simplified, schematic piping diagram of a microbial deactivation apparatus 10 illustrating one embodiment of the present invention.

A panel 22, that is part of a housing structure (not shown), defines a recess or cavity 24 dimensioned to receive items or instruments to be microbially deactivated. In the embodiment shown, a tray or container 26 is provided to receive the devices or instruments to be deactivated. Container 26 is dimensioned to be received within recess or cavity 24, as illustrated in FIG. 1.

A manually operable lid 32 is movable between an opened position allowing access to cavity 24, and a closed position (shown in FIG. 1) closing or covering cavity 24. A seal element 34 surrounds cavity 24 and forms a fluid-tight, i.e., an airtight and liquid-tight, seal between lid 32 and panel 22 when lid 32 is in a closed position. Latch means (not shown) are provided for latching and securing lid 32 in a closed position during a deactivation cycle. Cavity 24 essentially defines a chamber 36 when lid 32 is in a closed position.

A fluid circulation system 40 provides the microbial deactivation fluid to chamber 36 and is further operable to circulate the microbial deactivation fluid through chamber 36. Fluid circulation system 40 includes a water inlet line 42 that is connected to a source of heated water (not shown). A pair of filter elements 44, 46 are provided in water inlet line 42 to filter large contaminants that may exist in the incoming water. Filters 44, 46 are size exclusion filter elements, which remove particles of a certain size. Filter element 46 preferably filters out smaller particles than filter element 44. Filter element 44 preferably filters out particles of about 3 microns ($\mu$) or larger, and filter element 46 preferably filters out particles of about 0.1 microns ($\mu$) or larger. Pressure sensors (not shown) may be provided to monitor pressure drops across filter elements 44, 46, a change in the pressure drop across a filter element being indicative of clogging, rupturing or the like. Basically, filter elements 44, 46 are provided to filter out particles found in the water source used to supply apparatus 10. A viral reduction device 52 for inactivating organisms within the water source is preferably provided in water inlet line 42. Viral reduction device 52 is preferably an ultraviolet (UV) treatment device, and more preferably a class A device, as defined by NSF/ANSI Standards 55, or equivalent, although other viral reduction devices are contemplated. In one embodiment, a UV light system manufactured by Wedeco Ideal Horizons of Charlotte, N.C., having a minimum dosage of 40,000 $\mu W/cm^2$, is used. In the embodiment shown, viral reduction device 52 is shown downstream from filter elements 44, 46. It is contemplated that viral reduction device 52 could be disposed in water inlet line 42 upstream of filter elements 44, 46.

A water valve 54 controls the flow of water from water inlet line 42 to a system feeder line 62. System feeder line 62 includes a filtration system 100 to filter microscopic organisms and particles from the incoming water so as to provide microbially deactivated or sterile water to fluid circulation system 40. System feeder line 62 splits into a first branch feeder line 64 and a second branch feeder line 66. First branch feeder line 64 communicates with container 26 within chamber 36. Second branch feeder line 66 is connected to chamber 36 itself. A secondary branch feeder line 68 splits off of first branch feeder line 64 and is directed to the inlet portion of chemical delivery dispensing container 72 that contains dry chemical reagents that, when combined with water, form the antimicrobial fluid used in the deactivation system. A valve 74 controls flow through first branch feeder line 64 and through secondary branch feeder line 68 to chemical dispensing container 72. Chemical dispensing container 72 is disposed within a well 76 formed within panel 22 of the housing. Flow restrictors 78 in second branch feeder line 66 and secondary branch feeder line 68 regulate fluid flow therethrough.

A branch return line 82 extends from chemical dispensing container 72 and is connected to a system return line 88. Likewise, branch fluid return lines 84, 86 extend from container 26 and chamber 36 respectively and are connected to system return line 88. System return line 88 connects back with water inlet line 42 and fluid feeder line 62, as illustrated in FIG. 1. A pump 92 is disposed within system return line 88. Pump 92 is operable to circulate fluid through fluid circulation system 40. A drain line 94 is connected to system return line 88. A drain valve 96 controls fluid flow to drain line 94.

Figure 2:
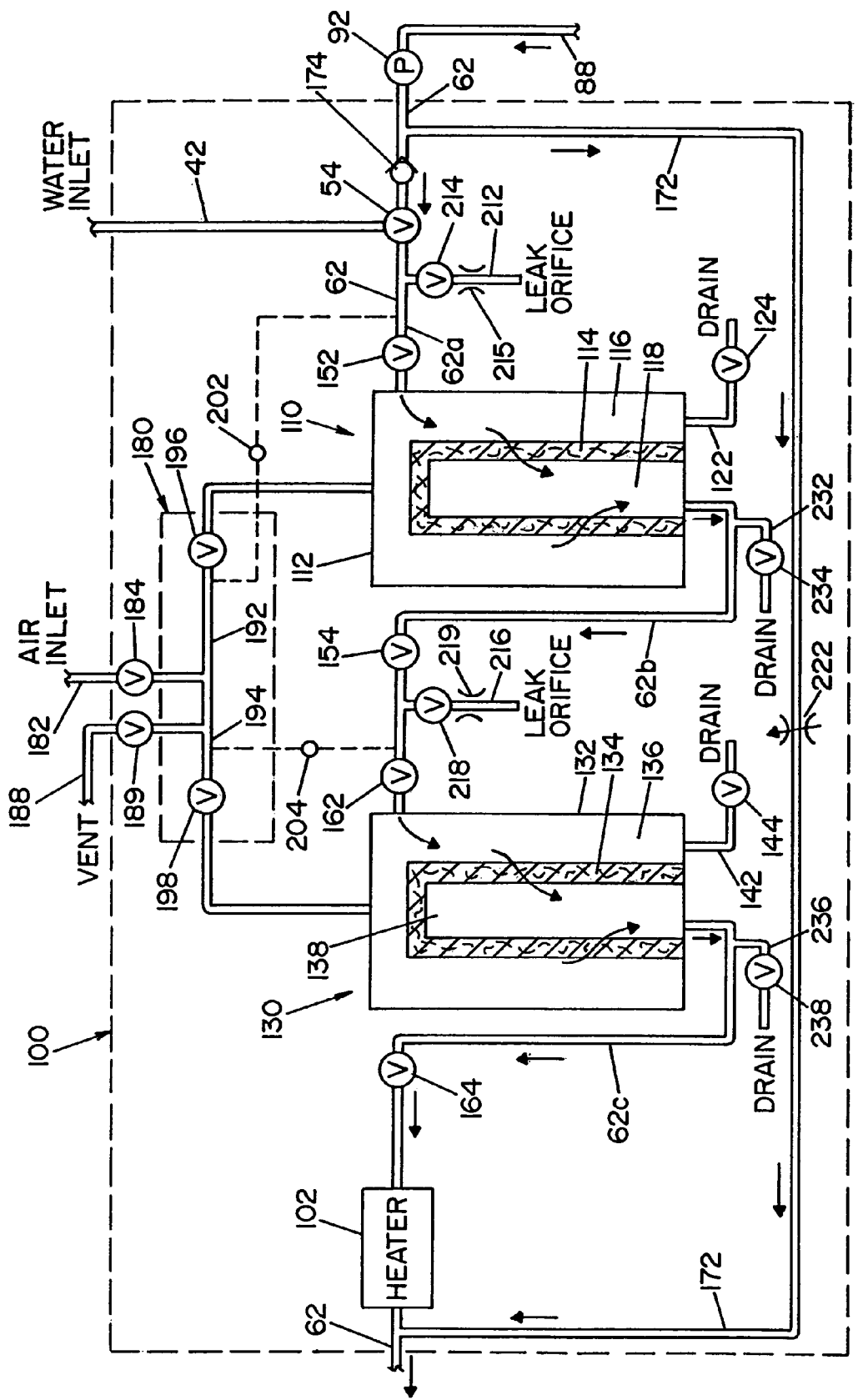
FIG. 2 is a schematic view of a filtration system, illustrating one embodiment of the present invention.

Referring now to FIG. 2, water filtration system 100 is best seen. Water filtration system 100 is disposed within fluid feeder line 62 and includes two filter elements 114 and 134, shown as part of filter assemblies 110, 130. Filter elements 114, 134 are disposed in series in fluid feeder line 62. A first section 62a of fluid feeder line 62 communicates water inlet line 42 to the inlet side of first filter assembly 110. A second section 62b of fluid feeder line 62 connects the outlet side of first filter assembly 110 to the inlet side of second filter assembly 130. A third section 62c of fluid feeder line 62 connects the outlet side of second filter assembly 130 to a heater 102 that is schematically illustrated in FIG. 2. Heater 102 is dimensioned to be able to heat water flowing through third section 62c of fluid feeder line 62 to a temperature of at least 95° C.

First filter assembly 110 includes housing 112 and an internal filter element 114. Filter element 114 is a bacterial retentive size exclusion filter that preferably filters out mycobacterium particles that are nominally 0.12 microns ($\mu$) or greater. Filter element 114 may include a cylindrical support layer (not shown), such as a polypropylene, a homopolymer surrounded by a filter membrane, such as a hydrophilic polyvinylidene difluoride (PVDF) or a polyethersulfone (PES) membrane. The filter membrane may be in the form of a capillary tube or hollow fiber member (or "fiber"), or in the form of a tubular sheath of a film formed either on the inner or outer surface of a tubular macroporous support, or a laminate sheet or film, or a laminate film deposited on the porous support. Suitable filter elements are obtainable from PTI Technologies of Oxnard, Calif.

Filter element 114 defines an annular outer chamber 116 and inner chamber 118. Outer chamber 116 represents the upstream, pre-filtration side of filter element 114, and inner chamber 118 of the filter assembly represents the downstream, filtered side of filter element 114. As shown in the drawings, first section 62a of fluid feeder line 62 communicates with outer chamber 116 of first filter assembly 110, and second section 62b of feeder line 62 communicates with inner chamber 118 of first filter assembly 110. A drain line 122 communicates with outer chamber 116 of first filter assembly 110. Valve 124 is disposed within drain line 122 to regulate flow from first filter assembly 110 to a drain.

Second filter assembly 130 includes housing 132 and an internal filter element 134. Filter element 134 is a bacterial retentive size exclusion filter that preferably filters out mycobacterium particles that are nominally 0.12 microns (μ) or greater. Filter element 134 may include a cylindrical support layer, such as a polypropylene, a homopolymer surrounded by a filter membrane, such as a hydrophilic polyvinylidene difluoride (PVDF) or a polyethersulfone (PES) membrane. The filter membrane may be in the form of a capillary tube or hollow fiber member (or "fiber"), or in the form of a tubular sheath of a film formed either on the inner or outer surface of a tubular macroporous support, or a laminate sheet or film, or a laminate film deposited on the porous support. Suitable filter elements are obtainable from PTI Technologies of Oxnard, Calif. Filter element 134 defines an annular outer chamber 136 and inner chamber 138. Outer chamber 136 represents the upstream, pre-filtration side of filter element 134, and inner chamber 138 of filter assembly 130 represents the downstream, filtered side of filter element 134. As shown in the drawings, second section 62b of feeder line 62 communicates with outer chamber 136 of second filter assembly 130 and third section 62c of feeder line 62 communicates with inner chamber 138 of second filter assembly 130. Drain line 142 communicates with outer chamber 136 of second filter assembly 130. A valve 144 is disposed within drain line 142 to regulate flow from second filter assembly 130 to a drain.

Both first and second filter assemblies 110, 130 are preferably pre-sterilized or microbially deactivated, prior to installation, so that the contents of filter assemblies 110, 130 are free of microbial contaminants. As will be described in greater detail below, filter assemblies 110, 130 are microbially deactivated or sterilized during each subsequent processing phase.

A first pair of valves 152, 154 is disposed in fluid feeder line 62 to enable isolation of first filter assembly 110. In this respect, valve 152 is disposed within first section 62a of fluid feeder line 62 at the inlet side of first filter assembly 110, and valve 154 is disposed in feeder line section 62b at the outlet side of first filter assembly 110. Similarly, a second pair of valves 162, 164 is provided in fluid feeder line 62 to enable isolation of second filter assembly 130. In this respect, valve 162 is disposed in fluid line section 62b at the inlet side of second filter assembly 130, and valve 164 is provided in fluid feeder line section 62c at the outlet side of second filter assembly 130.

A filter bypass line 172 communicates with fluid feed line 62 on opposite sides of first and second filter assemblies 110, 130. Specifically, one end of bypass line 172 is connected to fluid feed line 62 between pump 92 and the location where water inlet line 42 connects to fluid feed line 62. A directional check valve 174 is disposed between water inlet line 42 and filter bypass line 172 to prevent incoming water from communicating with filter bypass line 172, as shall be described in greater detail below. The other end of filter bypass line 172 communicates with feeder line 62 beyond filter assemblies 110, 130 and heater 102.

In accordance with another aspect of the present invention, a filter purge manifold system 180 is provided. Filter purge manifold system 180 is comprised of air inlet line 182 that is operable to provide clean, filtered, pressurized air to circulation system 40. A control valve 184 is disposed within air inlet line 182 to regulate the flow of air therethrough. The air in air inlet line 182 is preferably at a predetermined, regulated pressure. In this respect, air inlet line 182 may include a pressure regulator (not shown) for maintaining a generally constant, desired air pressure within air inlet line 182. Air inlet line 182 splits into two branch return lines 192, 194. A vent line 188 with control valve 189 is connected to branch return lines 192, 194, as illustrated in FIG. 2. Vent line 188 is provided to allow release of air from water filtration system 100 during a fill cycle, as shall be described in greater detail below.

First branch line 192 extends through housing 112 of first filter assembly 110 and communicates with outer chamber 116 of first filter assembly 110. Control valve 196 in first branch line 192 regulates the flow of air therethrough. Second branch line 194 extends through housing 132 of second filter assembly 130 and communicates with outer chamber 136 of second filter element assembly 130. A control valve 198 is disposed within branch line 194 to regulate flow therethrough.

A first pressure sensor 202 is provided across first section 62a of system feeder line 62 and branch line 192 to sense pressure on the upstream side of filter element 114.

A second pressure differential sensor 204 is provided across second section 62b of system feeder line 62 and branch line 194 to sense pressure on the upstream side of filter element 134.

A first leak orifice line 212 is connected to first section 62a of fluid feed line 62 between the water inlet valve 54 and valve 152 on the upstream side of first filter assembly 110. A valve 214 within leak orifice line 212 regulates flow therethrough. A flow restrictor 215 is disposed in leak orifice line 212 to regulate flow therethrough.

A second leak orifice line 216 is connected to second section 62b of fluid feed line 62 between valve 154 on the outlet side of first filter assembly 110 and valve 162 on the inlet side of second filter assembly 130. Valve 218 within leak orifice 216 regulates flow therethrough. A flow restrictor 219 is disposed in leak orifice line 216 to regulate flow therethrough. A drain line 232 is connected to section 62b of system feeder line 62 on the downstream side of filter element 114. A valve 234 regulates flow therethrough. A drain line 236 is connected to section 62c of system feeder line 62 on the downstream side of filter element 134. A valve 238 regulates flow therethrough.

A system microprocessor (not shown) controls the operation of circulation system 40 and the valves therein, as shall be described in greater detail below. The operation of circulation system 40 includes a fill phase, a chemical generation and exposure phase, a drain phase, one or more rinse phases, and a filter check phase, as shall also be described in greater detail below.

The present invention shall now further be described with reference to the operation of apparatus 10 and water filtration system 100. One or more items to be microbially deactivated or sterilized, such as medical, dental, pharmaceutical, veterinary or mortuary instruments or other devices are loaded into chamber 36. In the embodiment shown, the items would be loaded into container 26, which in turn would be placed into chamber 36. The items may be supported in a tray, basket, cartridge or the like (not shown) within chamber 36 or container 26.

The items are microbially deactivated or sterilized with a microbial deactivation fluid, such as a peracetic acid solution, which in one embodiment is formed by exposing and mixing dry chemical reagents within the chemical dispensing device 72 with incoming water. In this respect, at the beginning of a deactivation or sterilization operation, drain valve 96 in circulation system 40 is closed, and water valve 54 in inlet line 42 is opened to allow heated water to enter circulation system 40. Incoming water is first filtered by filter elements 44, 46 in water inlet line 42 that, as indicated above, remove particles above a certain size. Filter elements 44, 46 are sized to successively filter out smaller sized particles. Incoming water is then treated by a viral reduction device 52 that applies ultraviolet (UV) radiation to the water to inactivate organisms therein. The incoming water passes through the valve 54 and enters circulation system 40. The incoming water is then filtered by filter assemblies 110, 130 in feeder line 62 and proceeds to fill circulation system 40, chamber 36 and container 26.

Check valve 174 between water inlet valve 54 and filter bypass line 172 causes all of the incoming water to flow through the first and second filter assemblies 110, 130, thereby insuring filtration of the water flowing into apparatus 10.

The incoming water is under pressure from an external source, and forces air in fluid circulation system 40, chamber 36 and container 26 to an over-flow/air device (not shown) that is typically disposed at the highest point of apparatus 10. Air within the system migrates toward the over-flow device.

The presence of the water flowing through the over-flow block is indicative that apparatus 10 is filled with water. The system controller then causes water valve 54 to close, thereby stopping the flow of water into apparatus 10, i.e., into fluid circulation system 40, chamber 36 and container 26. The foregoing description basically describes a water fill phase of apparatus 10.

Once apparatus 10 is filled, the system controller initiates a generation and exposure phase of operation, wherein pump 92 is energized to circulate water through circulation system 40, chamber 36 and container 26. Valve 74 in first branch feeder line 64 is opened to create flow through chemical dispensing container 72. The water and dry chemical reagents within chemical dispensing container 72 form a microbial deactivation fluid that, as indicated above, in one embodiment of the invention, is peracetic acid. The deactivation fluid formed from the dry chemical reagents flows into circulation system 40, wherein it is circulated through circulation system 40, chamber 36 and container 26 by pump 92. In this respect, as indicated in the drawings, a portion of the microbial deactivation or steriliant fluid flows into chamber 36 around container 26 and a portion of the microbial deactivation fluid flows into and through container 26 and the items contained therein.

As indicated by the arrows in FIG. 2, a portion of the circulated deactivation fluid flows through filter bypass line 172 and a portion of the deactivation fluid flows through feed line 62 through filter assemblies 110, 130. The amount of fluid flowing through the respective portions of the system may be controlled by a regulating valve 222 disposed within filter bypass line 172 or fluid feed line 62. Preferably, a major portion of the deactivation fluid flows through filter bypass line 172. The portion of the deactivation fluid flowing through filter feed line 62 and through the first and second filter assemblies 110, 130 is preferably such to insure deactivation of filter elements 114, 134 by exposure to the deactivation fluid. In this respect, the flow of the deactivation fluid through filter assemblies 110, 130 microbially deactivates or sterilizes filter elements 114, 134 and inactivates any microbial contamination that may have entered into filter assemblies 110, 130 during the water fill phase. Thus, during each operation of apparatus 10, filter elements 114, 134 are exposed to a microbial deactivation or steriliant fluid to microbially deactivate or sterilize same. Moreover, the microbial deactivation fluid that flows throughout the closed-loop, fluid circulation system 40 during a deactivation phase, effectively decontaminates fluid circulation system 40, and the components and fluid conduits forming the same. In other words, fluid circulation system 40 is decontaminated during each decontamination cycle.

After a predetermined exposure period, a drain phase is initiated. Drain valve 96 is opened and the microbial deactivation fluid is drained from the re-circulation system, chamber 36 and container 26.

After the microbial deactivation fluid has been drained from apparatus 10, one or more rinsing phases is performed to rinse any residual microbial deactivation fluid and any residual matter from the deactivated items. In this respect, inlet valve 54 is opened to introduce fresh water into apparatus 10, in a manner as heretofore described as the fill phase. All incoming water passes water filtration system 100 wherein water entering circulation system 40 and chamber 36 is microbially deactivated or sterile. After each rinse fill, the rinse water is drained from apparatus 10 as heretofore described. Pump 92 may be activated to circulate the rinse water through apparatus 10. During each fill, circulation and drain phase, the fluid over-flow/air make-up assembly operates to prevent microbial contaminants from entering the internal environment within the system.

Following the rinse phase(s), first and second filter assemblies 110, 130 undergo a filter integrity test to insure that both first and second filter assemblies, and more specifically, filter elements 114, 134 are operating properly. Prior to conducting the filter integrity test, the filter housings 112, 132 are preferably drained by first closing valves 152, 154, 164 thereby isolating valve assemblies 110, 130 from filtration system 100 and from each other, and then opening valves 124, 144, 234 and 238 in drain lines 122, 142, 232 and 236, respectively. Valves 189, 196 and 198 are opened to allow vent air to filter housings 112, 132 to facilitate draining thereof. As will be appreciated, incoming air is filtered by filter means (not shown) to prevent contaminants from entering filter assemblies 110, 130. When filter assemblies are drained, drain valves 124, 144 and vent valve 189 are closed.

Water filtration system 100 is then tested for any leak(s) and to insure that leak orifices 212, 216 are not clogged or obstructed. In this respect, each filter assembly 110, 130 and associated connections define a "test area." Basically, the "test area" for first filter assembly 110 is defined by filter assembly 110 and the tubing or pipe connections between valves 54, 124, 154, 196 and 234. Similarly, the "test area" for second filter assembly 130 is defined by filter assembly 130 and the tubing or pipe connections between valves 154, 144, 238, 164 and 198. To conduct the leak test, valves 54, 154 and 164 remain closed to isolate first and second filter assemblies 110, 130 from fluid circulation system 40 and from each other. Valves 124, 144, 234 and 238 in lines 122, 142, 232 and 236, respectively, are closed to close-off any outlets from filter housings 112, 132, respectively. Valves 152, 162 are in an opened position. Valves 196, 198 are initially closed. Valve 184 in air inlet line 182 is then opened. As indicated above, the air pressure in air inlet line 182 is maintained at a set pressure level. Valves 196 and 198 in branch lines 192, 194, respectively, are then opened to expose the "test areas" to the set pressure. Once the pressure in the respective test areas stabilizes, valves 196 and 198 are closed thereby isolating the respective test areas from air inlet line 182. Pressure differential sensors 202, 204 compare the pressure within the test areas to the set pressure within air inlet line 182. If no leaks exist in the test pressure area, no difference in pressure should be sensed by first and second pressure differential sensors 202, 204. No change in pressure is indicative of no leaks within filter housings 112, 132 or the test pressure areas associated therewith. Valves 214 and 218 in leak orifice lines 212, 216 are then opened to allow the "set pressure" to leak or vent from the respective test pressure areas. First and second pressure differential sensors 202, 204 will sense a change in the differential pressure between the respective test pressure areas and the set pressure within air inlet line 182. This pressure change is indicative that leak orifices 212, 216 are not clogged or obstructed. No change in the differential pressure between a test area and the set pressure in air inlet line 182 is indicative that the leak orifice in the test area is clogged.

Following the aforementioned test to determine the integrity of the test area and the proper operation of the leak orifices, a water filter integrity test is conducted. According to one embodiment, the filter integrity test is a two-step process. In this respect, valves 54, 154 and 164 are closed to isolate first and second filter assemblies 110, 130 from fluid circulation system 40 and from each other. Valves 152, 162 are in an opened position. Valves 124, 144, 234, 238 in drain lines 122, 142, 232, 236 are closed. Valves 214, 218 in leak orifice lines 212, 216 are closed.

Valve 184 in air inlet 182 is then opened to allow pressurized air in branch lines 192, 194. As indicated above, the air pressure in air inlet line 182 is maintained at a set pressure level. Valves 196, 198 in feeder lines 192, 194 are then opened to allow pressurized air into the respective test areas associated with each filter assembly 110, 130. After a predetermined period of time wherein pressure in the respective test areas stabilizes at the aforementioned set pressure level, valves 196, 198 are closed.

With the pressure within the respective test areas stabilized to the "set pressure," valves 234, 238 in drain lines 232, 236 respectively, and valves 214, 218 in leak orifice lines 212, 216 are opened. As will be appreciated, a pressure differential will then exist across filter elements 114, 134 and through flow restrictions 215, 219 in leak orifice lines 212, 216. In other words, lower pressure exists in inner chamber 118, 138 of filter assemblies 110, 130 because valves 234, 238 connect inner chamber 118, 138 to drain. Likewise, leak orifice lines connect to the atmosphere, thereby establishing a lower pressure beyond flow restrictions 215, 219. The higher pressure in outer chambers 116, 136 slowly dissipates through filter elements 114, 134 and through flow restriction 215, 219 of leak orifice lines 212, 216. Differential pressure sensors 202, 204 sense the difference in pressure between the inner chambers 118, 138, and the set pressure level in line 182. The system controller monitors the change in pressure differential over time and determines a pressure drop per unit time $Q_{sys}$ for each respective test area. $Q_{sys}$ is the pressure drop per unit time caused by the pressure dissipating through filter elements 114, 134 and leak orifice lines 212, 216. Measuring the rate of change of pressure through filter elements 114, 134 and through leak orifice lines 212, 216, represent the first step in the two-step filter check.

Upon completion of the first step, valves 214, 218 in leak orifice lines 212, 216, and valves 234, 238 in drain lines 232, 236 are closed. Valves 196, 198 are then opened to re-establish the set pressure level in the respective test areas for filter assemblies 110, 130. Valves 196, 198 are then closed. Valves 234, 238 in drain lines 232, 236 are then opened. Valves 214, 218 in leak orifice lines 212, 216 remain closed. The system controller monitors over time the change in pressure differential senses by differential pressure transducers 202, 204 as pressure dissipates through filter elements 114, 134. In this respect, the second step of the filter check process repeats the first step, but with leak orifices 215, 219 closed. The system controller monitors the change in pressure differential over time and determines a pressure drop per unit time $Q_{filter}$ for each respective test area. $Q_{filter}$ is the pressure drop per unit time caused by pressure dissipating through a filter element alone.

With the foregoing data, the system controller determines whether the pressure changes are indicative of proper flow through filter elements 114, 134. In this respect, the system controller determines the difference between $Q_{sys}$ and $Q_{filter}$. This difference represents a pressure drop per unit of time $Q_{orif}$ of the leak orifice only. The system controller then determines a unit of pressure per volume value, CAL, by dividing $Q_{orif}$ by $Q_{cal}$. $Q_{cal}$ is a calibrated volumetric flow rate of the leak orifice at the desired test, i.e., set pressure. The CAL value is the relationship between the volumetric flow rate of the orifice and the corresponding pressure drop caused to the system in units of pressure per volume. A calculated, diffusion-of-flow rate, $Q_{calc}$, for a respective water filter element is then determined by dividing $Q_{swf}$ by CAL. The calculated value is the calculated, diffusion-of-flow rate of the filter based upon the filter pressure drop and the orifice. An abnormal pressure change is indicative that a defect exists in a filter elements 114, 134, thereby indicating the need for replacement of filter assembly 110 or filter assembly 130, and that a sterile or microbially deactivated operation may not have been performed by apparatus 10. In this respect, the failure of filter element 114 or filter element 134 is indicative that water may not have been filtered to a desired level and that contaminated water may have entered chamber 36. While the operation of one of the two filter elements 114, 134 is believed to provide sufficient filtration to insure microbially deactivated or sterile water, it is preferred that apparatus 10 indicate a faulty operation in the event that it senses even one defective filter element 114 or 134.

Although the foregoing leak test, leak orifice integrity test and filter integrity test were generally described as occurring simultaneously, it is contemplated that such tests for the respective filter assemblies 110, 130 and associated test areas could be performed independently.

The present invention thus provides a water filtration system 100 for use in a sterilant or microbial deactivation reprocessor that reduces the likelihood of microbial contamination being introduced into a chamber 36 by the incoming water.

Figure 3:
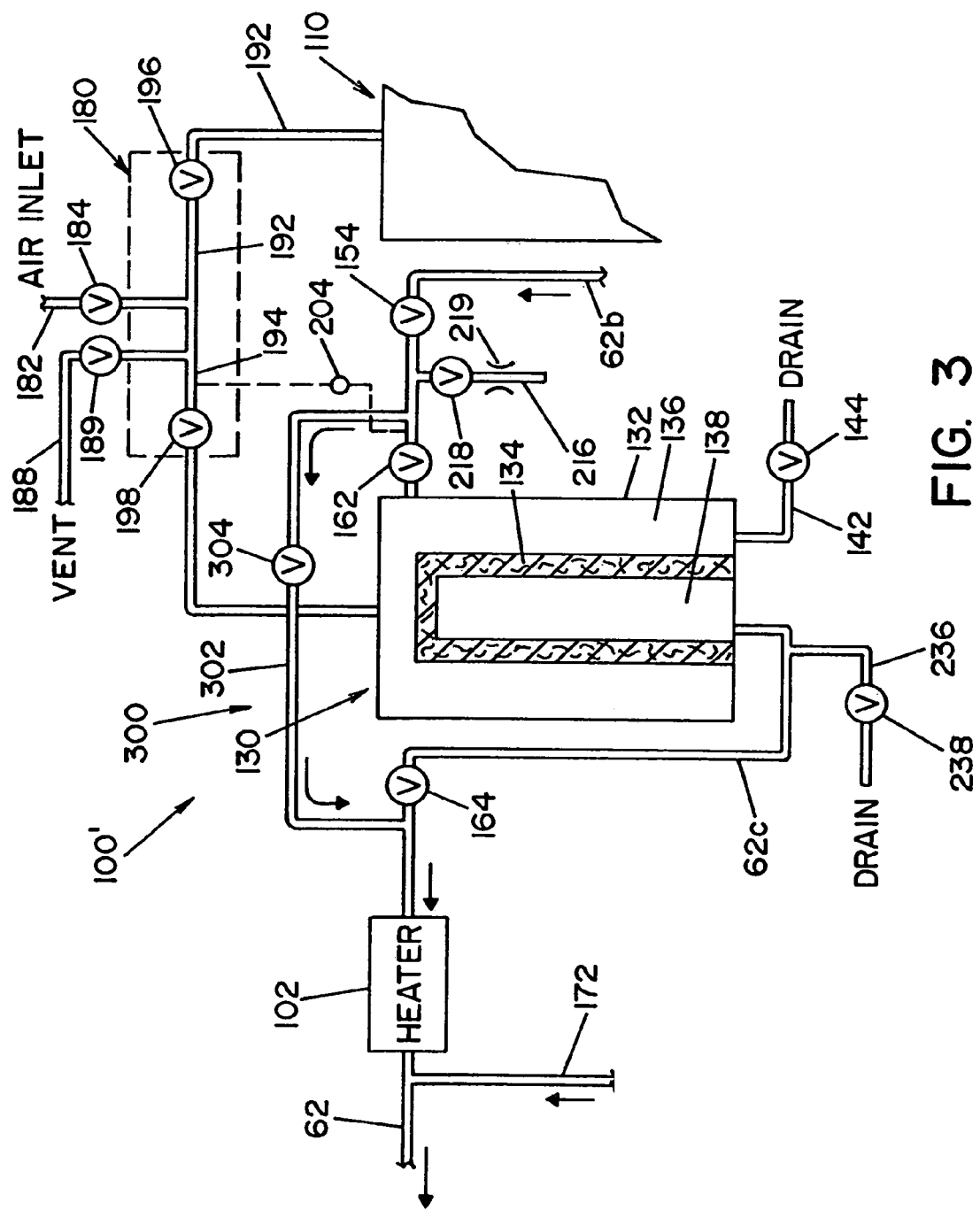
FIG. 3 is a partial view of the filtration system shown in FIG. 2, showing an alternate embodiment thereof.

Referring now to FIG. 3, a water filtration system 100' according to an alternate embodiment of the present invention is shown. Basically, FIG. 3 shows a bypass system 300 to allow second filter assembly 130 to be bypassed during a processing phase. In this respect, it is believed that the microbial deactivation fluid can degrade certain filter elements rendering it less effective for water purification. For example, surfactants present in the microbial deactivation fluid may cause a filter to become blocked, particularly if the filter pore size is extremely small. Accordingly, it may be desirable to limit the exposure of second filter assembly 130 to the deactivation fluid. In the embodiment shown, a bypass line 302 is connected at one end to second section 62b of fluid feeder line 62, and at its other end to third section 62c of fluid feeder line 62. A valve 304 controls the flow through bypass line 302. Valve 304 is a normally closed valve thereby blocking flow through bypass line 302 when fluid flows through second filter assembly 130. Second filter assembly 130 may be bypassed by closing valves 162, 164 and by opening valve 304 in bypass line 302 thereby causing fluid flowing through the fluid feeder line to bypass second filter assembly 130. The embodiment in FIG. 3 is controlled by the system controller to operate during a microbial deactivation fluid generation and circulation phase thereby preventing the deactivation fluid from flowing through second filter assembly 130. During a water inlet phase or a rinse phase, the controller would control the respective valves 304, 162, 164 to allow the incoming water to flow through second filter assembly 130 thereby providing sterile or microbially deactivated water for each fill and rinse phase.

Figure 4:
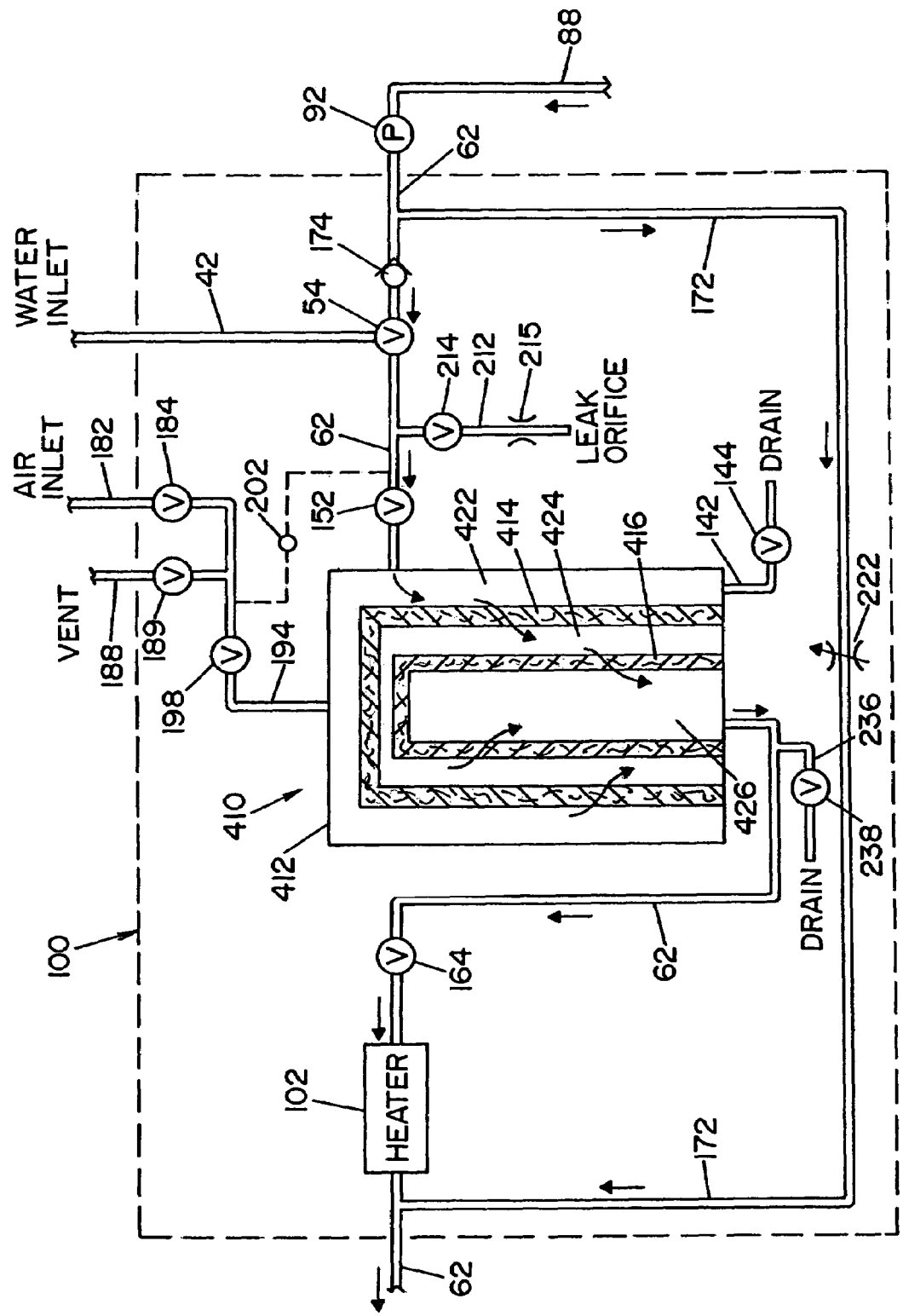
FIG. 4 is a schematic view of a filtration system, illustrating yet another embodiment of the present invention.

Referring now to FIG. 4, an alternate embodiment of water filtration system 100 having a single filter assembly 410 is shown. Filter assembly 410 includes a housing 412 and two (2) internal filter elements 414, 416. Both filter elements 414 and 416 are bacteria-retentive, size exclusion filters that preferably filter out mycobacterium particles that are nominally 0.12 microns ($\mu$) or greater. Filter elements 414, 416 may include cylindrical support layers (not shown), such as polypropylene, a homopolymer surrounded by a filter membrane, such as a hydrophilic polyvinylidene difluoride (PVDF) or a polyethersulfone (PES) membrane. The filter membrane may be in the form of a capillary tube or hollow fiber member (or "fiber"), or in the form of a tubular sheet of a film formed either on the inner or outer surface of a tubular macro porous support, or a laminate sheet or film, or a laminate film deposited on the porous support. An annular outer chamber 422 is defined between outer filter element 414 and housing 412. An intermediate chamber 424 is defined between outer filter element 414 and inner filter element 416. An inner chamber 426 is defined by filter element 416. As illustrated in FIG. 4, filter assembly 410 is disposed in system feeder line 62. Drain line 142 communicates with outer chamber 422, and drain line 236 communicates with inner chamber 426.

As illustrated by the arrows in FIG. 4, fluid flowing through system feeder line 62 flows first through outer filter element 414 and then through inner filter element 416. In this respect, inner filter 416 is down line from outer filter element 414. Accordingly, filter assembly 410 provides the same filtering effects as the embodiment shown in FIG. 2. However, the single filter assembly 410 reduces the number of valves and connections of water filtration system 100 thereby increasing the reliability and performance thereof. In addition to simplifying the overall structure, eliminating a filter cartridge and reducing the number of connecting lines, the overall volume of circulation system 40 is thereby reduced, thereby reducing the amount of liquid chemistry required within the system. It will also be appreciated that the aforementioned leak test, leak orifice integrity test and filter integrity test may likewise be conducted on filter assembly 410 and an associated "test area."

The foregoing description is a specific embodiment of the present invention. It should be appreciated that this embodiment is described for purposes of illustration only, and that numerous alterations and modifications may be practiced by those skilled in the art without departing from the spirit and scope of the invention.

In accordance with another embodiment of the present invention, heater 102 in third section 62c of fluid feeder line 62 is operated to heat water flowing through section 62c to a temperature sufficient to inactivate viruses in water that has passed through first and second filter assemblies 110, 130. As indicated above, viral reduction device 52, that is preferably an ultraviolet (UV) treatment device, treats incoming water to inactivate organisms therein. Heater 102 is utilized as a second viral reduction device in conjunction with, or as an alternative to, viral reduction device 52. In this respect, heater 102 also treats incoming water to inactivate organisms therein. In one embodiment of the present invention, water flowing through third section 62c of fluid feeder line 62 is heated by heater 102 to a temperature between about 40° C. and about 95° C. In another embodiment of the present invention, the water flowing through third section 62c of fluid feeder line 62 is heated to a temperature between about 55° C. and about 85° C. In a more preferred embodiment, the water is heated to a temperature between about 75° C. and about 85° C.

Preferably, heater 102 is used as a viral reduction device only during a rinse phase(s) of the decontamination cycle. In this respect, water entering circulation system 40 and chamber 36 during a fill phase is microbially decontaminated or sterilized as a result of the sterilizing chemicals introduced into the water from chemical delivery dispensing container 72 during the chemical generation and exposure phase of the operation of circulation system 40. Accordingly, any viral contamination existing within water in apparatus 10 is inactivated by such chemicals. Because no deactivating chemicals or sterilants are introduced into the rinse water, heater 102 is utilized to inactivate any viruses that may be present in the water following filtration by first and second filter assemblies 110, 130 before such water enters chamber 36 during a rinse phase(s). In this manner, the sterility of the instruments within chamber 36 is further ensured.

While heater 102 is preferably used to inactivate viruses during a rinse phase(s) of the decontamination cycle, it would be appreciated that heater 102 may also be used to heat water entering chamber 36 during the chemical generation and exposure phases. In this respect, the decontaminating properties of chemicals introduced by chemical dispensing container 72 may be enhanced by heating such chemicals during the chemical generation and exposure phases of the operating cycle.

Heater 102 can also be used to heat fluid circulating through fluid circulation system 40 during the deactivation phase during which fluid circulates through fluid circulation system 40.

It is intended that all such modifications and alterations be included insofar as they come within the scope of the invention as claimed or the equivalents thereof.

Having described the invention, the following is claimed:

1. A method of operating a sterilizer having a chamber for receiving items to be sterilized, a fluid circulation system for circulating fluids through said chamber, means for generating a liquid sterilant from dry chemical reagents by mixing water therewith, and a water filtration system for filtering water entering said sterilizer, said filtration system including: a fluid feed line that is attached to said chamber, a directional valve disposed in said fluid feed line, a first filter element in said fluid feed line, for filtering fluids therethrough, said first filter element located between said directional valve and said chamber and downstream of said directional valve, a second filter element in said fluid feed line for filtering fluids flowing therethrough, said second filter element located between said first filter element and said chamber, a water line connected to said fluid feed line at an intersection located between said directional valve and said first filter element, and a bypass line connected to said fluid feed line to define a fluid path that bypasses said directional valve and said first and second filter elements, said method of operating comprising the steps of:

filling said sterilizer with water from a water source, by passing said water through said first and second filter elements;

generating a liquid sterilant by mixing water filtered by said first and second filter elements with said dry chemical reagents;

circulating said liquid sterilant through said fluid circulation system and said filtration system wherein a portion of said liquid sterilant is directed through said first and second filter elements, and a portion is directed through said bypass conduit;

draining said sterilizer after a predetermined exposure time;
passing water for rinsing from said water line through said first and second filter elements;
heating said water for rinsing after said water for rinsing has passed through said first and second filter elements; and
introducing said water for rinsing into said chamber.

2. A method of operating a sterilizer as defined in claim 1, wherein said second filter element is capable of filtering smaller particles than said first filter element.

3. A method of operating a sterilizer as defined in claim 1, further comprising the step of exposing said water for rinsing to UV radiation before said water for rinsing passes through said first and second filter elements.

4. A method of operating a sterilizer as defined in claim 1, further comprising the step of testing the integrity of said filter elements after each sterile processing phase.

5. A method of operating a sterilizer as defined in claim 1, wherein said water for rinsing is heated to a temperature of from about 40° C. to about 95° C.

6. A method of operating a sterilizer as defined in claim 1, wherein said water for rinsing is heated to a temperature of from about 55° C. to about 85° C.

7. A method of operating a sterilizer as defined in claim 1, wherein said water for rinsing is heated to a temperature of from about 75° C. to about 85° C.

8. A method of operating a reprocessor having a chamber for receiving items to be microbially deactivated, a fluid circulation system for circulating fluids through said chamber, means for generating a microbial deactivation fluid from dry chemical reagents by mixing water therewith, and a water filtration system for filtering water entering said reprocessor, said filtration system including: a fluid feed line connectable to a source of pressurized water, a first filter element and a second filter element in said fluid feed line, said second filter element disposed in said fluid feed line downstream from said first filter element, and a bypass line connected to said fluid feed line to define a fluid path that bypasses said first and second filter elements, said water filtration system being connected to said fluid circulation system, said method of operating comprising the steps of:
filling said reprocessor with water from a water source, by passing said water through said first and second filter elements;
generating a microbial deactivation fluid by mixing water filtered by said first and second filter elements with said dry chemical reagents;
circulating said microbial deactivation fluid through said fluid circulation system and said filtration system wherein a portion of said microbial deactivation fluid is directed through said fluid feed line and another portion is directed through said first filter element and said second filter element;
draining said reprocessor after a predetermined exposure time;
filling said reprocessor with water for rinsing, by passing said water for rinsing through said first and second filter elements; and
heating said water for rinsing prior to introduction of said water for rinsing into said chamber.

9. A method of operating a reprocessor as defined in claim 8, wherein said second filter element is capable of filtering smaller particles than said first filter element.

10. A method of operating a reprocessor as defined in claim 8, further comprising the step of exposing said water to UV radiation before said water for rinsing passes through said first and second filter elements.

11. A method of operating a reprocessor as defined in claim 8, further comprising the step of testing the integrity of said filter elements after each microbially deactivated processing phase.

12. A method of operating a reprocessor as defined in claim 8, wherein said water for rinsing is heated to a temperature of from about 40° C. to about 95° C.

13. A method of operating a reprocessor as defined in claim 8, wherein said water for rinsing is heated to a temperature of from about 55° C. to about 85° C.

14. A method of operating a reprocessor as defined in claim 8, wherein said water for rinsing is heated to a temperature of from about 75° C. to about 85° C.

15. A method of operating a reprocessor having a chamber for receiving items to be microbially deactivated, a fluid circulation system for circulating fluids through said chamber, means for generating a microbial deactivation fluid from dry chemical reagents by mixing water therewith, and a water filtration system for filtering water entering said reprocessor, said filtration system including: a fluid feed line connectable to a source of pressurized water, a first filter element and a second filter element in said fluid feed line, said second filter element being downstream from said first filter element, a heater being downstream of said first and said second filter elements and a bypass line connected to said fluid feed line to define a fluid path that bypasses said first and second filter elements and said heater, said water filtration system being connected to said fluid circulation system, said method of operating comprising the steps of:
filling said sterilizer with water from a water source, by passing said water through said first and second filter elements;
generating a liquid sterilant by mixing said filtered water with said dry chemical reagents;
circulating said liquid sterilant through said fluid circulation system and said filtration system wherein a portion of said liquid sterilant is directed through said fluid feed line and another portion is directed through said first filter element and said second filter element to produce filtered liquid sterilant; and
operating said heater during said circulating step.

16. A method of operating a sterilizer as defined in claim 15, wherein said second filter element is capable of filtering smaller particles than said first filter element.

17. A method of operating a reprocessor as defined in claim 15, further comprising the step of exposing said water to UV radiation before said water passes through said first and second filter elements.

18. A method of operating a reprocessor as defined in claim 15, further comprising the step of testing the integrity of said filter elements after each microbially deactivated processing phase.

19. A method of operating a reprocessor as defined in claim 15, wherein said water for rinsing is heated to a temperature of from about 40° C. to about 95° C.

20. A method of operating a reprocessor as defined in claim 15, wherein said water for rinsing is heated to a temperature of from about 55° C. to about 85° C.

21. A method of operating a reprocessor as defined in claim 15, wherein said water for rinsing is heated to a temperature of from about 75° C. to about 85° C.

22. A method of operating a reprocessor as defined in claim 15, wherein said heater is operated to heat said filtered water during said step of filling said sterilizer.

23. A method of operating a reprocessor as defined in claim 22, further comprising the step of exposing said water to UV radiation before said water passes through said first and second filter elements.

24. In a reprocessor having a circulation system for circulating a liquid sterilant or microbial deactivation fluid through a chamber that forms a part of said circulation system, a water filtration system for filtering water used in said reprocessor, said water filtration system, comprising:
  a fluid feed line forming a portion of said circulation system, one end of said fluid feed line in fluid communication with said chamber;
  a directional valve disposed in said fluid feed line;
  a first filter element disposed in said fluid feed line for filtering fluids flowing therethrough, said first filter element located upstream from said chamber;
  a second filter element disposed in said fluid feed line for filtering fluids flowing therethrough, said second filter element located between said first filter element and said chamber;
  a water line connectable to a source of pressurized water, said water line connected to said fluid feed line at a location between said directional valve and said first filter element; and
  a bypass line connected to said fluid feed line to define a fluid path that bypasses said first and second filter elements, said bypass line connected at one end to said fluid feed line upstream of said directional valve and connected at another end to said fluid feed line between said second filter element and said chamber.

25. A reprocessor as defined in claim 24, further comprising valve means operable to isolate said first and second filter elements from said circulation system and from each other.

26. A reprocessor as defined in claim 24, further comprising means for determining the integrity of said first and second filter elements.

27. A reprocessor as defined in claim 26, wherein said means for determining the integrity of said first and second filter elements includes a first differential pressure sensing device operable to sense a pressure differential across said first filter element, and a second differential pressure sensing device operable to sense a pressure differential across said second filter element.

28. A reprocessor as defined in claim 27, wherein said means for determining the integrity of said first and second filter elements includes:
  means for isolating each filter element from said filtration system,
  means for pressurizing the upstream side of each of said isolated filter elements, and
  means for determining the integrity of each filter element based upon the rate of the pressure drop through said isolated filter element over time.

29. A reprocessor as defined in claim 24, wherein said first and second filter elements are disposed within a single filter housing.

30. A reprocessor as defined in claim 24, wherein said first and second filter elements are disposed within separate filter housings and said second filter housing is downstream from said first filter housing.

31. A reprocessor as defined in claim 24, wherein said second filter element is capable of filtering smaller particles than said first filter element.

32. A reprocessor as defined in claim 24, wherein all water entering said reprocessor from said water line first passes through said filter elements, and a portion of all fluid circulated through said circulation system passes through said fluid feed line and said filter elements.

33. A method of operating a sterilizer having a chamber for receiving items to be sterilized, a fluid circulation system for circulating fluids through said chamber, means for generating a liquid sterilant from dry chemical reagents by mixing water therewith, and a water filtration system for filtering water entering said sterilizer, said filtration system including: a fluid feed line that is attached to said chamber, a directional valve disposed in said fluid feed line, a first filter element disposed in said fluid feed line for filtering fluids therethrough, said first filter element located between said directional valve and said chamber and downstream of said directional valve, a second filter element disposed in said fluid feed line for filtering fluids flowing therethrough, said second filter element located between said first filter element and said chamber, a water line connected to said fluid feed line at an intersection located between said directional valve and said first filter element, and a bypass line connected to said fluid feed line to define a fluid path that bypasses said directional valve and said first and second filter elements, said method of operating comprising the steps of:
  filling said sterilizer with water from a water source, by passing said water through said first and second filter elements;
  generating a liquid sterilant by mixing water filtered by said first and second filter elements with said dry chemical reagents; and
  circulating said liquid sterilant through said fluid circulation system and said filtration system wherein a portion of said liquid sterilant is directed through said first and second filter elements, and a portion is directed through said bypass conduit.

34. A method of operating a sterilizer as defined in claim 33, further comprising the step of exposing said water to UV radiation before said water passes through said first and second filter elements.

35. A method of operating a sterilizer as defined in claim 33, wherein a step of testing the integrity of said filter elements follows the circulating step.

36. A method of operating a sterilizer as defined in claim 33, wherein said second filter element is capable of filtering smaller particles than said first filter element.

37. In a reprocessor having a chamber for receiving items to be microbially deactivated or sterilized, a fluid circulation system for circulating fluids through said chamber, means for generating a microbial deactivation fluid from dry chemical reagents by mixing water therewith, and a water filtration system for filtering water entering said reprocessor, said filtration system including: a fluid feed line connectable to a source of pressurized water, a first filter element and a second filter element in said fluid feed line, said second filter element being downstream from said first filter element, a method of checking the integrity of at least one of said filter elements, comprising the steps of:
  a) establishing a first known pressure on the upstream side of said filter element;
  b) allowing pressure on said upstream side of said filter element to dissipate through said filter element and through a leak orifice of known dimensions;
  c) monitoring over time the change in pressure on the upstream side of said filter;
  d) establishing a second known pressure on the upstream side of said filter element;
  e) allowing pressure on said upstream side of said filter element to dissipate through said filter element;

f) monitoring over time the change in pressure on the upstream side of said filter; and g) determining a flow rate through said filter based on the changes in pressure determined in steps c) and f).

38. A method as defined in claim 37, further comprising the step of conducting a pressurized leak test prior to step a).

39. A method as defined in claim 37, further comprising the step of conducting a test on said leak orifice prior to step a).

40. A method as defined in claim 37, wherein the change in pressure on the upstream side of said first and second filter elements is accomplished by using a first and second differential pressure sensing device, said first differential pressure sensing device measuring the difference in the pressure between the upstream side of said first element and the pressure in a control pressure zone, said second differential pressure sensing device measuring the difference in the pressure on the upstream side of said second element to the pressure in said control pressure zone.

41. A method as defined in claim 37, wherein said second filter element is capable of filtering smaller particles than said first filter element.

* * * * *